(12) United States Patent
Romano et al.

(10) Patent No.: US 12,048,553 B2
(45) Date of Patent: Jul. 30, 2024

(54) MEDICAL ANALYZER USING MIXED MODEL INVERSIONS

(71) Applicant: The Government of the United States of America, as represented by the Secretary of the Navy, Arlington, VA (US)

(72) Inventors: Anthony J Romano, Washington, DC (US); William G. Szymczak, Potomac, MD (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 442 days.

(21) Appl. No.: 16/848,244

(22) Filed: Apr. 14, 2020

(65) Prior Publication Data

US 2020/0323479 A1 Oct. 15, 2020

Related U.S. Application Data

(60) Provisional application No. 62/833,897, filed on Apr. 15, 2019.

(51) Int. Cl.
*A61B 5/00* (2006.01)
*A61B 5/055* (2006.01)
(Continued)

(52) U.S. Cl.
CPC .......... *A61B 5/4064* (2013.01); *A61B 5/0042* (2013.01); *A61B 5/055* (2013.01);
(Continued)

(58) Field of Classification Search
CPC ..... A61B 5/4064; A61B 5/0042; A61B 5/055; G01R 33/30; G01R 33/50; G01R 33/5608; G01R 33/56341; G01R 33/56358
See application file for complete search history.

(56) References Cited

U.S. PATENT DOCUMENTS 8,842,896 B2 * 9/2014 Hajnal ............ G01R 33/56341
382/131
2013/0131490 A1 * 5/2013 Huston, III ...... G01R 33/56358
600/410
(Continued)

OTHER PUBLICATIONS

Kunimatsu A, Aoki S, Masutani Y, Abe O, Hayashi N, Mori H, Masumoto T, Ohtomo K. The optimal trackability threshold of fractional anisotropy for diffusion tensor tractography of the corticospinal tract. Magn Reson Med Sci. Apr. 1, 2004;3(1):11-7. doi: 10.2463/mrms.3.11. PMID: 16093615. (Year: 2004).*
Romano A, Szymczak W, Okamoto R, et al. Moderate to Severe TBI Studies Using Mixed Model Inversions. 1st International MRE Workshop;. 2017 (Year: 2017).*
(Continued)

*Primary Examiner* — Christopher Koharski
*Assistant Examiner* — James F McDonald
(74) *Attorney, Agent, or Firm* — US Naval Research Laboratory; William P. Ladd (57) ABSTRACT

Systems and methods are provided for medical diagnosis and analysis using mixed model inversions. For example, a medical analyzer using mixed model inversions according to an embodiment of the present disclosure can be used to diagnose traumatic brain injury (TBI), which allows for isotropic and anisotropic inversions to be performed, enabling more accurate information about brain stiffness to be obtained.

17 Claims, 6 Drawing Sheets

(51) Int. Cl.
    *G01R 33/30* (2006.01)
    *G01R 33/50* (2006.01)
    *G01R 33/56* (2006.01)
    *G01R 33/563* (2006.01)

(52) U.S. Cl.
    CPC .............. *G01R 33/30* (2013.01); *G01R 33/50* (2013.01); *G01R 33/5608* (2013.01); *G01R 33/56341* (2013.01)

(56) References Cited

U.S. PATENT DOCUMENTS

2014/0316245 A1* 10/2014 Romano .............. A61B 5/4064
                                                                  600/410
2016/0356873 A1* 12/2016 Topgaard ........... G01R 33/5608

OTHER PUBLICATIONS

Xu et al., The ellipsoidal area ratio: an alternative anisotropy index for diffusion tensor imaging, Magnetic Resonance Imaging, vol. 27, Issue 3, 2009, pp. 311-323, ISSN 0730-725X https://doi.org/10.1016/j.mri.2008.07.018. (Year: 2009).*

Webster, J.G. and Descoteaux, M. (2015). High Angular Resolution Diffusion Imaging (HARDI). In Wiley Encyclopedia of Electrical and Electronics Engineering, J.G. Webster (Ed.). https://doi.org/10.1002/047134608X.W8258 (Year: 2015).*

Yin Z, Romano AJ, Manduca A, Ehman RL, Huston J 3rd. Stiffness and Beyond: What MR Elastography Can Tell Us About Brain Structure and Function Under Physiologic and Pathologic Conditions. Top Magn Reson Imaging. Oct. 2018;27(5):305-318. doi: 10.1097/RMR.0000000000000178 (Year: 2018).*

* cited by examiner

MEDICAL ANALYZER USING MIXED MODEL INVERSIONS

CROSS REFERENCE TO RELATED APPLICATIONS

This application claims the benefit of U.S. Provisional Patent Application No. 62/833,897, filed on Apr. 15, 2019, which is incorporated by reference herein in its entirety.

FEDERALLY SPONSORED RESEARCH AND DEVELOPMENT

The United States Government has ownership rights in this invention. Licensing inquiries may be directed to Office of Technology Transfer at US Naval Research Laboratory, Code 1004, Washington, DC 20375, USA; +1.202.767.7230; techtran@nrl.navy.mil, referencing Navy Case Number 107858-US3.

FIELD OF THE DISCLOSURE

This disclosure relates to medical analysis systems, including medical diagnosis systems.

BACKGROUND

Current methods for the diagnosis of the state of health of the human brain include imaging techniques such as Computerized Tomography (CT), Magnetic Resonance Imaging (MRI), Positron Emission Tomography (PET), Functional MRI (fMRI), X-rays, and blood tests. While these imaging and chemical methodologies are able to provide visual and metabolic information, they cannot provide metrics such as stiffness which have been shown to be indicative and sensitive to changes in brain health. Additionally, humans are prone to error and visually evaluating images using the methodologies outlined above can often lead to inconclusive or incorrect conclusions. Also, contrast between healthy and diseased areas are often not distinguished between each other using only these imaging modalities.

BRIEF DESCRIPTION OF THE DRAWINGS/FIGURES

The accompanying drawings, which are incorporated in and constitute part of the specification, illustrate embodiments of the disclosure and, together with the general description given above and the detailed descriptions of embodiments given below, serve to explain the principles of the present disclosure. In the drawings.

Features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

In the following description, numerous specific details are set forth to provide a thorough understanding of the disclosure. However, it will be apparent to those skilled in the art that the disclosure, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring aspects of the disclosure.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to understand that such description(s) can affect such feature, structure, or characteristic in connection with other embodiments whether or not explicitly described.

1. Overview

Embodiments of the present disclosure provide systems and methods for medical diagnosis and analysis using mixed model inversions. For example, a medical analyzer using mixed model inversions according to an embodiment of the present disclosure can be used to diagnose traumatic brain injury (TBI), which allows for isotropic and anisotropic inversions to be performed, enabling more accurate information about brain stiffness to be obtained. Gray matter has isotropic stiffness, and white matter is fibrous and therefore anisotropic.

Embodiments of the present disclosure use rotational optimization, which increases the accuracy of anisotropic inversion. Further, embodiments of the present disclosure use mixed model inversion, which uses fractional anisotropy to determine which procedures to perform (e.g., isotropic or anisotropic procedures). Further, embodiments of the present disclosure are optimized for parallel processing, leading to reduced diagnosis time.

Systems and methods according to embodiments of the present disclosure advantageously enable diagnosis to be performed without the intervention of a human, thereby alleviating potential error. Further, as the feature space of healthy controls grows, so does the reliability of the diagnosis. Embodiments of the present disclosure enable diagnosis of a myriad of diseases and conditions in seconds.

Further, currently most scientists use isotropic inversions only to determine brain stiffness, which homogenizes all structures together. Applying anisotropic inversions using DTI in accordance with an embodiment of the present disclosure leads to significantly better diagnosis of brain injury.

2. Performing Medical Analysis Using Mixed Model Inversions

Embodiments of the present disclosure use a combination of measurement modalities, such as magnetic resonance elastography (MRE) and diffusion tensor imaging (DTI), and a combination of operations, such as isotropic and anisotropic inversions, to aid in medical diagnosis. It is known that various diseases and trauma can lead to physical alterations of brain structure. Embodiments of the present disclosure use an evaluation of the stiffness of the brain regions to provide metrics for classification. This approach provides an improved noninvasive diagnostic capability for the evaluation of conditions of the brain such as Traumatic Brain Injury, Alzheimer's Disease, Amyotrophic Lateral Sclerosis, Post Traumatic Stress Disorder, and Parkinson's Disease, for example.

In an embodiment, MRE is utilized to obtain the elastic displacements throughout the brain, which is subjected to mild vibration induced, for example, by a pneumatic pillow actuator. In an embodiment, the patient lies in a prone position with their head inside a head coil, which is itself inside an MRI scanner.

In an embodiment, magnetic resonance imaging (MRI) is initially performed to obtain T1 and T2 images that provide a measurement of the internal structure of the brain, and DTI is subsequently performed to obtain the diffusion tensor, which measures the amount of diffusion of protons (e.g., indicating water) throughout the brain. In an embodiment, this enables the evaluation of a metric based on the eigenvalues of the diffusion tensor called fractional anisotropy (FA). With this metric, isotropic and anisotropic regions of the brain can be delineated. MRE can also be performed to obtain the orthogonal displacements through the brain that are being excited by the pillow actuator.

A medical analyzer in accordance with an embodiment of the present disclosure, provided with the T1 and T2 images, the DTI eigenvectors and eigenvalues, and the MRE displacement data, can perform isotropic and anisotropic inversions to evaluate the local stiffness throughout the brain. In an embodiment, in regions of the brain wherein FA is less than 0.2, the eigenvalues trace out spheres, and this indicates that the region is isotropic, meaning that the wave speed is the same in every direction, and an isotropic inversion analysis and/or procedure can be performed. In an embodiment, in regions of the brain wherein FA is greater than or equal to 0.2, the eigenvalues trace out ellipsoids, and this indicates that the region is anisotropic, meaning that there are three wave speeds in every direction, and an anisotropic inversion analysis and/or procedure can be performed. In an embodiment, an exemplary anisotropic inversion procedure performed by the medical analyzer uses an orthotropic anisotropic model including nine independent elastic coefficients.

In an embodiment, these inversions are performed with the aid of computers and run preferably in parallel for computational facility. Operations and/or algorithms used by a medical analyzer in accordance with an embodiment of the present disclosure are perfectly suited for parallel computation, as each location can be evaluated independently of the other. When spread over several thousand processors (such as provided by the Department of Defense (DOD) High Performance Computational platforms such as TOPAZ and Thunder), a full human brain can be analyzed in less than 15 minutes. Additionally, segmentation of the various isotropic and anisotropic structures of the brain can be performed to allow for the analysis of 145 specific structures, using 22 individual metrics based on both diffusion and stiffness. These data can then provide the feature space, which can then be utilized to train the classifier using, for example, K-Means Clustering and Linear Discriminant Analysis (LDA), K Nearest Neighbor (KNN), classifiers such as the K Support Vector Machine (KSVM), and/or the Relevance Vector Machine (RVM). Once trained on healthy controls, the results of age and gender matched patients can be compared to these features for rapid and dependable diagnosis.

3. Exemplary Medical Analyzer

Figure 1:
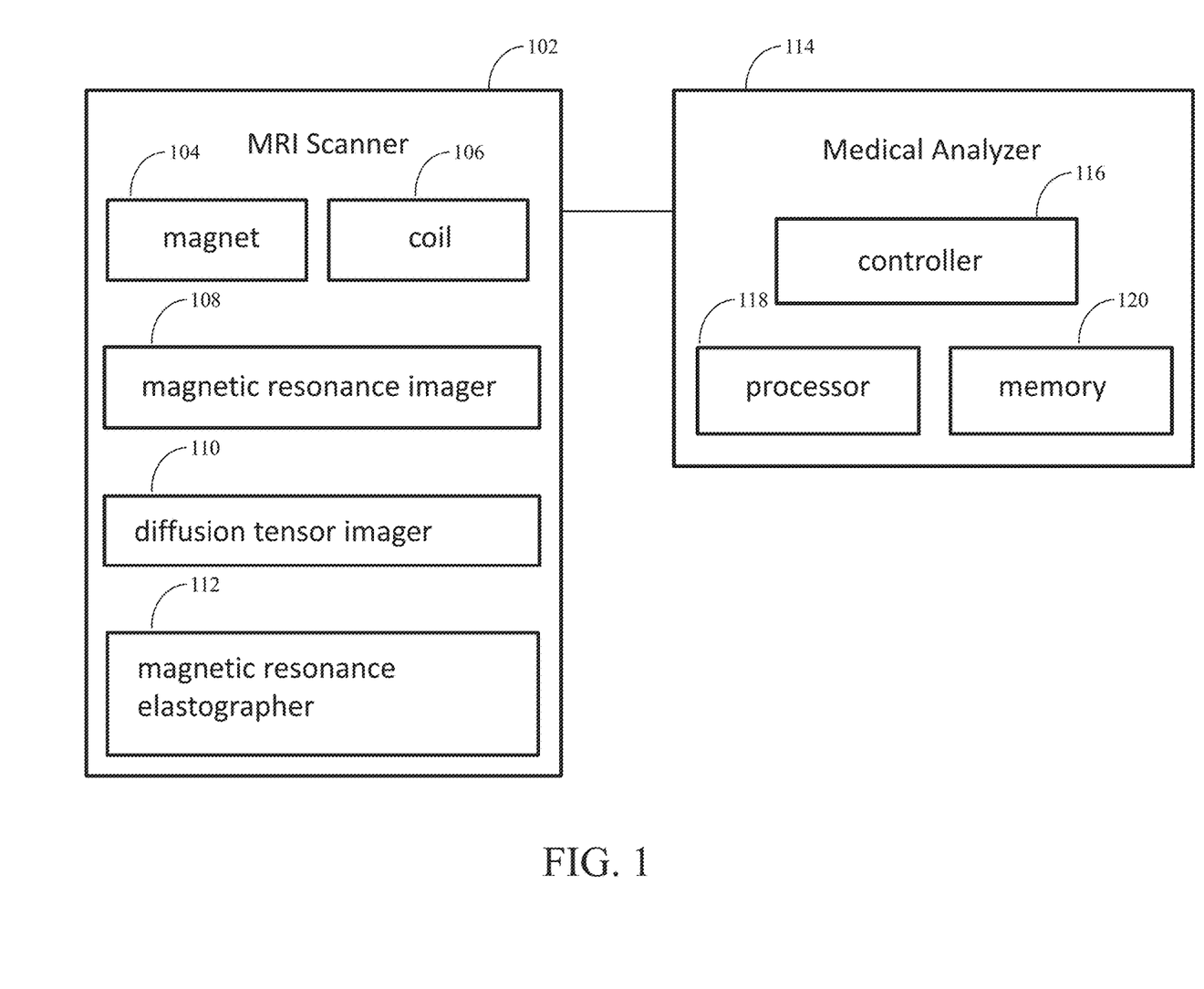
FIG. 1 is a diagram of an exemplary medical analyzer in accordance with an embodiment of the present disclosure.

FIG. 1 is a diagram of an exemplary medical analyzer in accordance with an embodiment of the present disclosure. FIG. 1 includes an MRI scanner 102 and a medical analyzer 114. In FIG. 1, MRI scanner includes at least one magnet 104, at least one coil 106, a magnetic resonance imager 108, a diffusion tensor imager 110, and a magnetic resonance elastographer 112. In an embodiment MRI scanner 102 also includes one or more processors or memories. In FIG. 1, medical analyzer 114 includes a controller 116, a processor 118, and a memory 120.

In an embodiment, a patient lies in MRI scanner 102 with his or her head inside coil 106. In an embodiment, MRI scanner 102 determines longitudinal and transverse precessions of atoms in the brain. In an embodiment, magnetic resonance imager 108 performs magnetic resonance imaging to obtain T1 (longitudinal relaxation) images and T2 (transverse relaxation) images using magnet 104. In an embodiment, MRI scanner 102 uses a phase contrast RF pulse and measures vibration of the skull (e.g., using a pneumatic oscillating driver) to determine local elastic displacements of the brain structures.

In an embodiment, magnet 104 polarizes the hydrogen nuclei within the tissue of the patient's brain and creates an oscillating magnetic field which is temporarily applied to the brain at appropriate resonance frequencies. The excited atoms emit a radio frequency (RF) signal which is measured by coil 106. In an embodiment, the RF signal can be processed to deduce position information by looking at the changes in RF level and phase caused by varying the local magnetic fiend using gradient coils. In an embodiment, the contrast between different tissues can be determined by the rate at which excited atoms return to their equilibrium state. In an embodiment, each tissue returns to its equilibrium state after excitation by the independent relaxation processes of T1 (longitudinal relaxation) and T2 (transverse relaxation). For example, T1 refers to the time it takes for tissue to go back to its natural state after being excited along the longitudinal direction, and T2 refers to the time it takes for tissue to go back to its natural state after being excited along the transverse direction. In an embodiment, magnetic resonance imager 108 processes these relaxation measurements, tissue structure, and location information and generates maps of the brain structures (e.g., T1 and T2 images).

In an embodiment, magnetic resonance elastographer 112 measures elastic vibration of the patient's brain using magnetic resonance elastography (MRE). In an embodiment, magnetic resonance elastographer 112 determines the elastic displacements throughout the patient's brain, which is subjected to mild vibration induced, for example, by a pneumatic pillow actuator.

In an embodiment, diffusion tensor imager 110 obtains the diffusion tensor for the patient's brain using diffusion tensor imaging, which measures the amount of diffusion of protons (e.g., indicating water) throughout the brain. In an embodiment, this enables the evaluation of the fractional anisotropy (FA) metric based on the eigenvalues of the diffusion tensor. In an embodiment, diffusion tensor imager 110 generates the eigenvectors and eigenvalues of the diffusion tensor and the FA metric. For example, in an embodiment, the FA metric is derived from eigenvalues of the diffusion tensor, and the fiber pathways are derived from the corresponding eigenvectors of the diffusion tensor.

In an embodiment, MRI scanner 102 transmits (e.g., over a wired or wireless connection) the T1 and T2 images generated by magnetic resonance imager 108, the DTI eigenvectors and eigenvalues and FA metric generated by diffusion tensor imager 110, and the MRE displacement data generated by magnetic resonance elastographer 112 to medical analyzer 114.

In an embodiment, medical analyzer 114 performs isotropic and anisotropic inversions to evaluate the local stiffness throughout the patient's brain based on the information received from MRI scanner 102. In an embodiment, in regions of the brain wherein FA is less than 0.2, the eigenvalues trace out spheres, and this indicates that the region is isotropic, meaning that the wave speed is the same in every direction, and medical analyzer 114 (e.g., in an embodiment, controller 116) performs isotropic inversion to obtain brain stiffness. In an embodiment, medical analyzer (e.g., controller 116) uses isotropic inversion to determine the transverse stiffness of the brain. For example, in an embodiment, to determine isotropic inversion, medical analyzer 114 determines the acceleration of the displacement of the brain tissue in a particular direction and divides this direction by the Laplacian of the displacement.

In an embodiment, in regions of the brain wherein FA is greater than or equal to 0.2, the eigenvalues trace out ellipsoids, and this indicates that the region is anisotropic, meaning that there are three wave speeds in every direction, and white matter pathways can be evaluated. In an embodiment, after determining that FA is greater than or equal to 0.2, medical analyzer 114 (e.g., in an embodiment, controller 116) performs anisotropic inversion to obtain brain stiffness. In an embodiment, medical analyzer (e.g., controller 116) uses anisotropic inversion to obtain anisotropic brain stiffness using the MRE data.

In an embodiment, these stiffness values can be observed to differ within the brains of healthy or diseased regions. Therefore, in an embodiment, medical analyzer 114 uses these stiffness values as diagnostic metrics for the evaluation of the state of health or pathology of the brain. For example, in an embodiment, medical analyzer 114 compares typical stiffness values of healthy controls with those of patients to determine the presence or absence of disease and/or injury in respective areas of the brain. In an embodiment, this procedure is called mixed-model inversion, since the value of FA can provide a binary, data driven decision method to indicate which inversion method should be utilized.

Magnetic resonance imager 108, diffusion tensor imager 110, magnetic resonance elastographer 112, and controller 116 can be implemented using hardware, software, and/or a combination of hardware and software in accordance with embodiments of the present disclosure. Portions of MRI scanner 102 can be implemented using a single device or multiple devices in accordance with embodiments of the present disclosure. Portions of medical analyzer 114 can be implemented using a single device or multiple devices in accordance with embodiments of the present disclosure.

In an embodiment, medical analyzer 114 is implemented as a separate standalone device that is configured to perform medical analysis based on the information received from MRI scanner 102. In an embodiment, medical analyzer 114 is integrated into a host device (e.g., a host computer) and perform medical analysis based on the information received from MRI scanner 102. Further, while processor 118 and memory 120 are shown integrated into medical analyzer 114 in FIG. 1, it should be understood that, in an embodiment, medical analyzer 114 does not have an integrated memory 120 and processor 118 but instead uses a processor and/or memory of a host device (e.g., a host computer).

Figure 2:
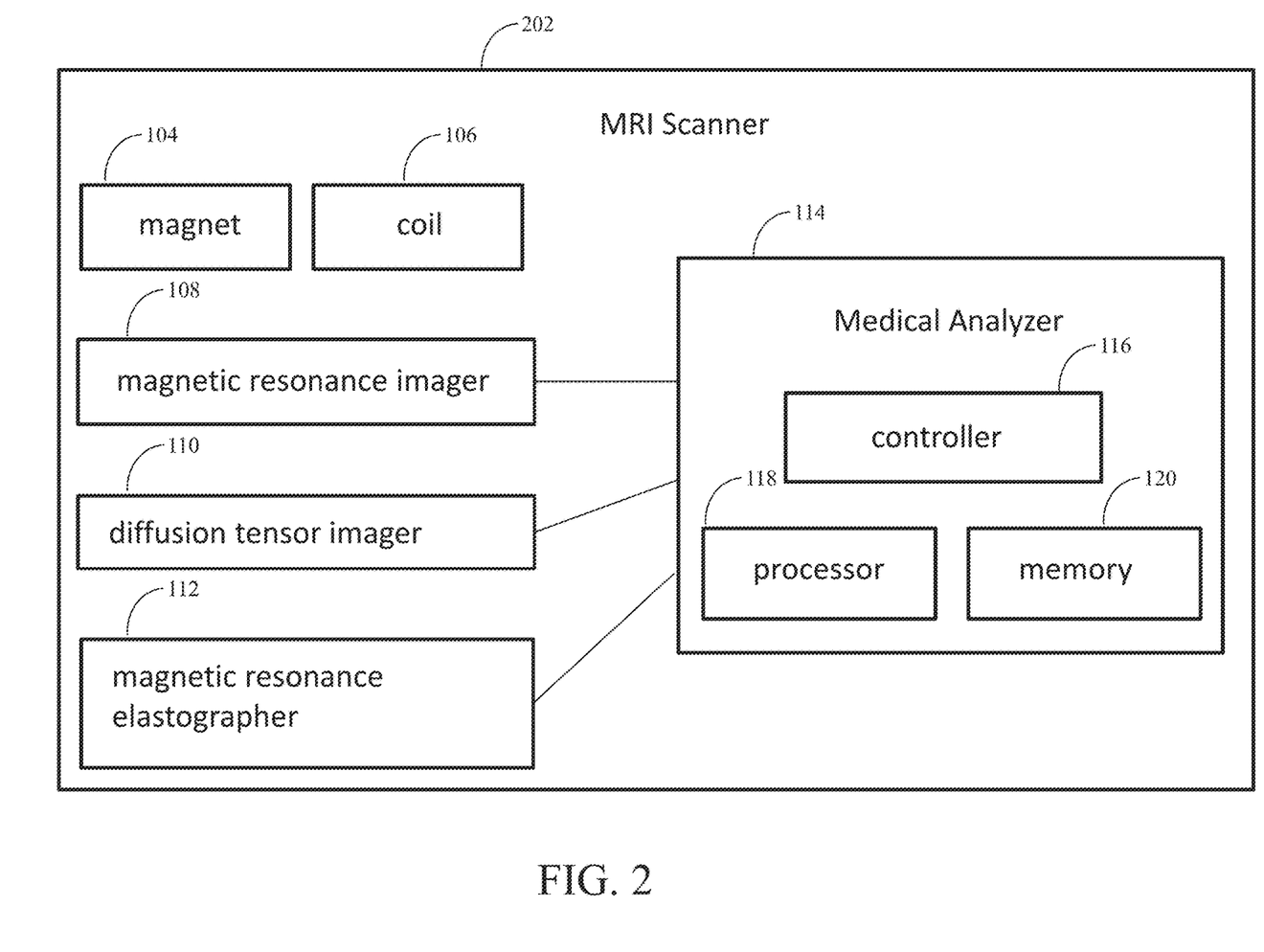
FIG. 2 shows another diagram of a MRI scanner 202 in accordance with an embodiment of the present disclosure.

In an embodiment, medical analyzer 114 can be implemented into an MRI scanner. FIG. 2 shows another diagram of a MRI scanner 202 in accordance with an embodiment of the present disclosure. In FIG. 2, MRI scanner 202 includes medical analyzer 114. For example, in an embodiment, medical analyzer 114 receives the T1 and T2 images generated by magnetic resonance imager 108, the DTI eigenvectors and eigenvalues and FA metric generated by diffusion tensor imager 110, and the MRE displacement data generated by magnetic resonance elastographer 112, determines brain stiffness, and classifies portions of the patient's brain as healthy or unhealthy. In an embodiment, processor 118 and memory 120 are not located inside medical analyzer 114 but are part of MRI scanner 202 and are shared by medical analyzer 114, magnetic resonance imager 108, diffusion tensor imager 110, and magnetic resonance elastographer 112.

4. Exemplary Methods for Medical Analysis Using Mixed Model Inversions

Figure 3:
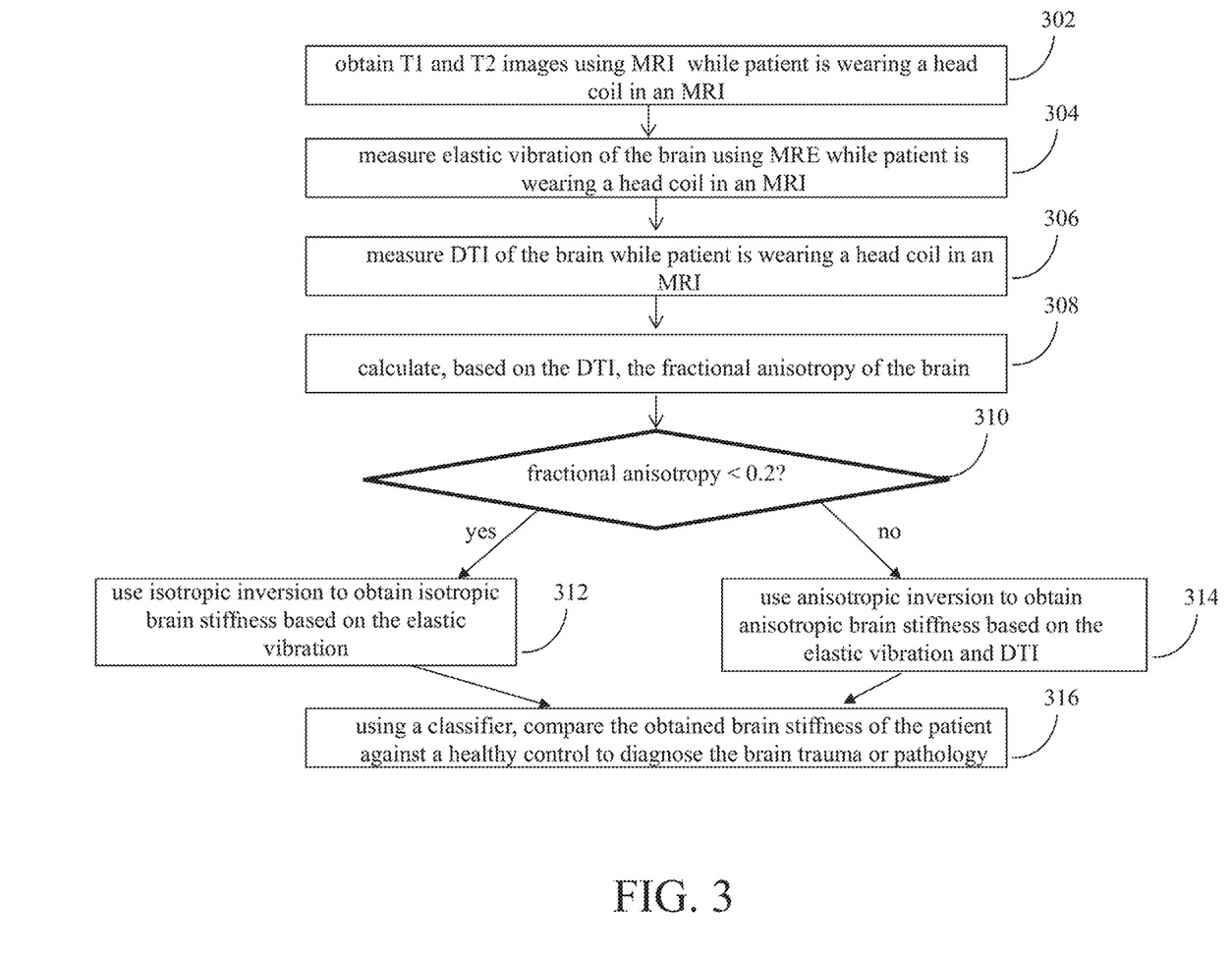
FIG. 3 is an exemplary flowchart of a method for non-invasively diagnosing brain injury using mixed model inversion in accordance with an embodiment of the present disclosure.

FIG. 3 is an exemplary flowchart of a method for noninvasively diagnosing brain injury using mixed model inversion in accordance with an embodiment of the present disclosure. In step 302, T1 and T2 images are obtained using MRI while a patient is wearing a head coil in an MRI. For example, in an embodiment, magnetic resonance imager 302 generates T1 and T2 images.

In step 304, elastic vibration of the brain is measured using MRE. For example, in an embodiment, magnetic resonance elastographer 112 generates MRE displacement data. In step 306, DTI of the brain is measured. For example, in an embodiment, diffusion tensor imager 110 generates DTI eigenvectors and eigenvalues. In step 308, the fractional anisotropy (FA) of the brain is calculated based on the DTI. For example, in an embodiment, diffusion tensor imager 110 calculates the FA value based on the DTI eigenvectors and eigenvalues.

In step 310, a determination is made regarding whether the FA is less than 0.2. For example, in an embodiment, MRI scanner 102 transmits the T1 and T2 images generated by magnetic resonance imager 108, the DTI eigenvectors and eigenvalues and FA metric generated by diffusion tensor imager 110, and the MRE displacement data generated by magnetic resonance elastographer 112 to medical analyzer 114, which determines whether the FA value is less than 0.2. In step 312, if a determination is made that the FA value is less than 0.2, isotropic inversion is used to obtain isotropic brain stiffness based on the elastic vibration (e.g., using an algorithm and/or a device that performs isotropic inversion). For example, in an embodiment, medical analyzer 114 (e.g., using controller 116) uses an isotropic inversion procedure to determine isotropic brain stiffness. In step 314, if a determination is made that the FA value is greater than or equal to 0.2, anisotropic inversion is used to obtain isotropic brain stiffness based on the elastic vibration and DTI (e.g., using an algorithm and/or a device that performs anisotropic inversion). For example, in an embodiment, medical analyzer 114 (e.g., using controller 116) uses an anisotropic inversion procedure to determine anisotropic brain stiffness. In step 316, the obtained brain stiffness of the patient is compared against a healthy control to diagnose the brain trauma or pathology. For example, in an embodiment, medical analyzer 114 (e.g., using controller 116) uses a classifier to compare the patient's brain stiffness against a healthy control to determine which regions of the brain are healthy and/or unhealthy.

5. Brain Structures and Metrics

In an embodiment, a fusion of measurement and analytical modalities are used by medical analyzer 114, which provide stiffness and diffusion of each of the 145 brain regions, providing more direct insight into alterations of the structural integrity of the different regions. As there is a significant difference in stiffness and diffusion in damaged or diseased brain regions when compared to those values of healthy controls, medical analyzer 114 provides more accurate indicators for damaged or diseased brain regions. For example, in ALS, we have found that the corticospinal tracts are significantly softer than those of healthy controls due to the effects of neurodegeneration of the myelin sheaths surrounding the axons. In regions of the brain that have been damaged due to concussion, entire brain structures can become much softer than surrounding tissue, while in mild TBI, regions that have been damaged can become significantly stiffer than healthy tissue. Additionally, brain tumors can often be either much stiffer or softer than the surrounding tissue. Such differences are not apparent in standard MRI scans. This is why MRE in combination with DTI and our analytical inversions are often called "noninvasive palpation."

There have been identified 145 individual brain structures ranging from isotropic, anisotropic, or a composite comprised of a combination of both of these types of structures. Table 1 below provides a list of 20 of the 145 brain structures.

TABLE 1

| 20 of 145 Segmented Brain Structures |
|---|
| CER, Cerebellum-LR |
| SF, SuperiorFrontal-LR |
| THA, Thalamus-LR |
| CCF, bundle, CC-Front |
| CAU, Caudate-LR |
| CCP, bundle, CC-Posterior |
| PUT, Putamen-LR |
| CCS, bundle, CC-Superior |
| PAL, Pallidum-LR |
| CG, Cingulum-LR |
| HIP, Hippocampus-LR |
| CPT, Corticopontine-LR |
| AMY, Amygdala-LR |
| CST, Corticospinal-LR |
| CLC, CaudalAnteriorCingulate-LR |
| FNX, Fornix-LR |
| LOF, LateralOrbitoFrontal-LR |

TABLE 1-continued

| 20 of 145 Segmented Brain Structures |
|---|
| PTR, PosteriorThalamusRad-LR |
| MOF, MedialOrbitoFrontal-LR |
| SFO, Superiorfronto-Occipital Fasc |

Using MRE and DTI, medical analyzer 114 obtains the elastic displacements and white matter pathways and analyzes them using isotropic and/or anisotropic inversion algorithms for the evaluation of their stiffness values. These quantities, along with diffusion quantities derived from T1, T2, and FA, are used as metrics for comparison to delineate between healthy and diseased brain regions. Therefore, this approach can be termed a non-invasive diagnostic tool for the evaluation of brain health or pathology.

In an embodiment, a mixed-model inversion (MMI) method for diagnosing traumatic brain injury in accordance with an embodiment of the present disclosure uses 22 metrics. Table 2 below provides MRI and diffusion metrics.

TABLE 2

| MRI and Diffusion Metrics |
|---|
| FA, Fractional Anisotropy |
| RA, Relative Anisotropy |
| VR, Volume Ratio |
| CL, Linear Anisotropy |
| CP, Planar Anisotropy |
| CS, Spherical Symmetry |
| CA, 1-CS |
| AD, Axial Diffusivity |
| MD, Mean Diffusivity |
| RD, Radial Diffusivity |
| T1W & T2W |

Table 3 below provides isotropic and anisotropic metrics (orthotropic stiffness metrics in kPa).

TABLE 3

| Isotropic and Anisotropic Metrics |
|---|
| MuG, Isotropic Shear Stiffness |
| C11, Anisotropic Longitudinal Stiffness ($x_1$) |
| C22, Anisotropic Longitudinal Stiffness ($x_2$) |
| C33, Anisotropic Longitudinal Stiffness ($x_3$) |
| C44, Anisotropic Shear Stiffness ($x_2$ & $x_3$) |
| C55, Anisotropic Shear Stiffness ($x_1$ & $x_3$) |
| C66, Anisotropic Shear Stiffness ($x_1$ & $x_2$) |
| C12, Anisotropic Longitudinal Stiffness ($x_{12}$) |
| C13, Anisotropic Longitudinal Stiffness ($x_{13}$) |
| C23, Anisotropic Longitudinal Stiffness ($x_{23}$) |

Figure 4:
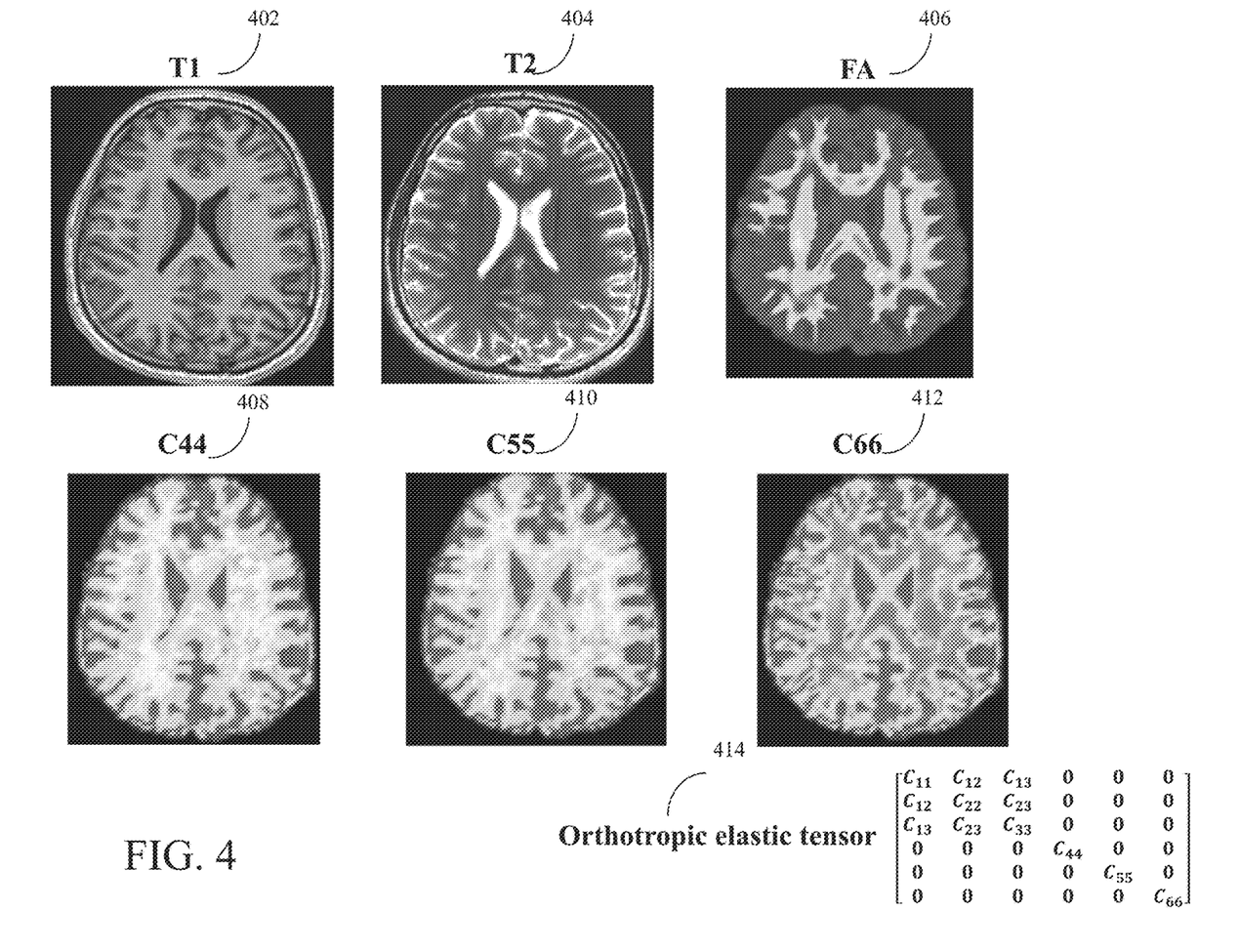
FIG. 4 shows of exemplary brain images and an exemplary orthotropic elastic tensor in accordance with an embodiment of the present disclosure.

FIG. 4 shows of exemplary brain images and an exemplary orthotropic elastic tensor in accordance with an embodiment of the present disclosure. Specifically, FIG. 4 shows a T1 image 402, a T2 image 404, an image showing the result of a FA operation 406, an image for the C44 metric 408, an image for the C55 metric 410, and an image for the C66 metric 412. FIG. 4 also shows exemplary orthotropic elastic tensor 414.

Figure 5:
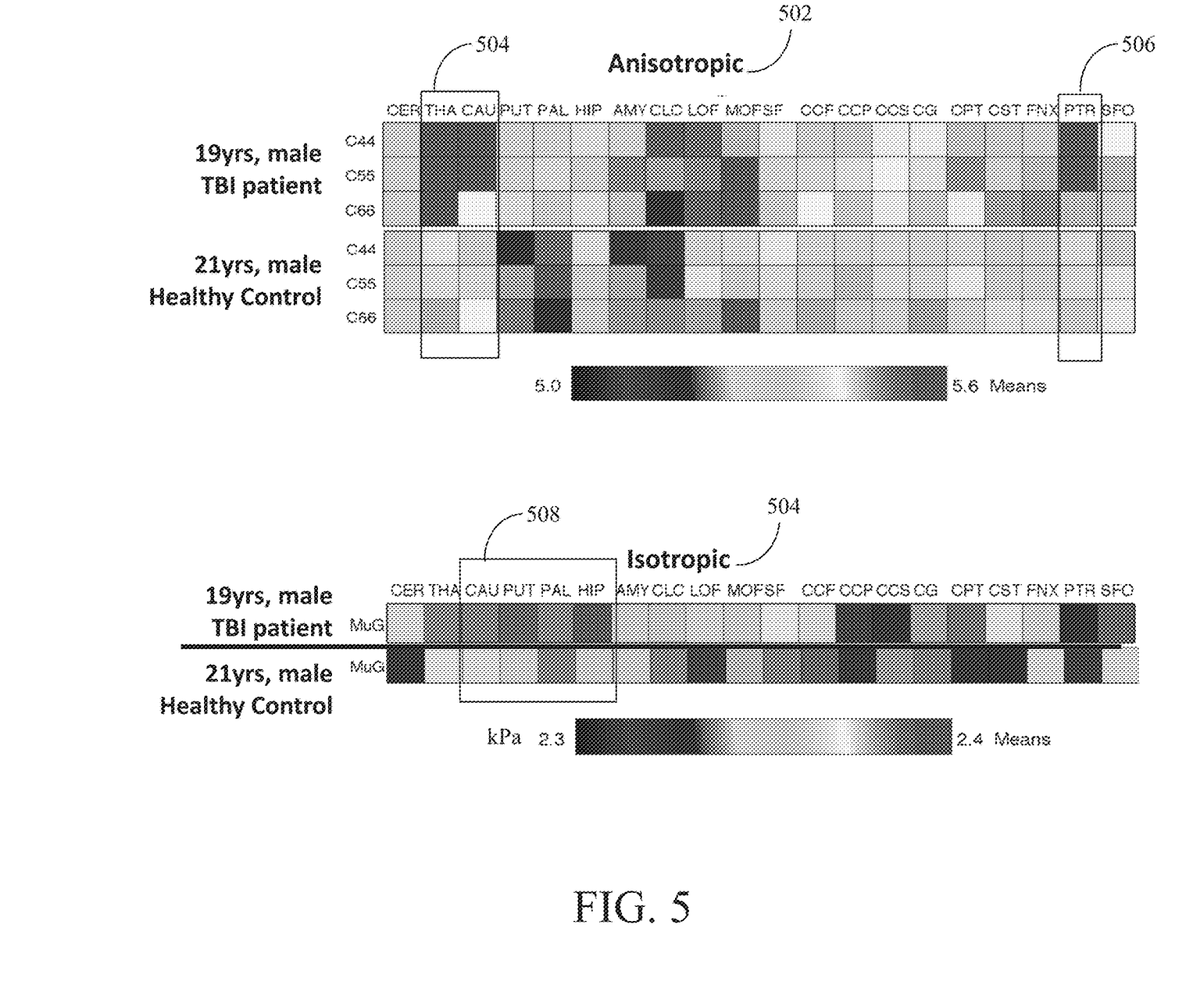
FIG. 5 shows an image indicating significant trauma regions based on analysis from medical analyzer 114 in accordance with an embodiment of the present disclosure.

FIG. 5 shows an image indicating significant trauma regions based on analysis from medical analyzer 114 in accordance with an embodiment of the present disclosure. The results of FIG. 5 are from a study of one 21 year old healthy male and one 19 year old male high school hockey player who had suffered a concussion and was diagnosed with diffuse axonal injury. It took approximately 17 minutes of execution time for a single, full brain for all coefficients.

In FIG. 5 boxes 504 and 506 indicate the presence of trauma regions based on anisotropic analysis 502, and rectangle 508 indicates the presence of trauma regions based on isotropic analysis 504.

6. Machine Learning Classification

In an embodiment, using the 22 metrics provided by diffusion measurements and isotropic and anisotropic stiffnesses obtained from the MMI, medical analyzer 114 uses classifier (e.g., in an embodiment, integrated into controller 116) to train based on the labeled data (the metrics of the healthy controls and prior-diagnosed patients), which are then compared to those of unlabeled age and gender matched patients for diagnostic purposes. These metrics supplement the isotropic stiffness and diffusion metrics.

Further, in an embodiment, medical analyzer 114 is not limited to determine TBI, but can also be used for other purposes. For example, in an embodiment, medical analyzer 114 can be used to determine the presence or absence of breast cancer. For example, in an embodiment, using the metrics discussed above, one option is to employ a feature space based on the Pearson Moments (mean, variance, Skew, etc.) of each of the metrics within a set of overlapping sub-regions of the breast to be used for the machine learning classifier of medical analyzer 114. The dimension of the feature space can be reduced using, for example, Principal Component Analysis (PCA), which transforms the feature space into one of mixed-metric vectors that minimize correlations using eigenvector decompositions.

Several classification protocols can be explored to determine which provides the best accuracy in patient identification, including: k-nearest neighbor classification, random forest classification, support vector machines, and relevance vector machines. Each protocol will be optimized over their input parameters, such as the number of nearest neighbors or the choice of kernel function for the vector machine classifiers.

The k-nearest neighbors algorithm for classification performs classification based on a set of k closest points in multidimensional feature space. Given a point in features space, the k-nearest points are used with either uniform weights or weights depending on the inverse distance to classify the point (e.g., healthy or tumorous).

The Random Forest Classifier is based on examining a number of decision tree classifiers on sub-samples of the training dataset. It is referred to as a "meta simulator" using averaging to improve its predictive accuracy and control over-fitting. Each decision tree (or regression tree) within the "forest" is a binary tree with each node splitting the feature space in two, and each of the leaves (terminal nodes) representing a specific diagnosis. The trees are generated using vectors generated from a random selection of features in the training space. The "Forest" represents a set of trees, (100 is a usual default), which are "polled" to determine a final classification.

A Support Vector Machine (SVM) Classifier is an algorithm which determines a lower dimensional decision surface to separate the feature space. It used the concept of a "margin" defined to be the smallest distance between the decision boundary and any of the samples in the training feature space. An SVM classifier will find the decision boundary that maximizes the margin. The shape of the decision surface is dependent on the "kernel" used for the optimization, where a kernel is a positive definite function of the distance between two feature space points, (e.g. Gaussian, Radial Basis Function, etc.) The "support vectors" are the subset of the training feature space points that determine the maximum margin.

The Relevance Vector Machine (RVM) technique is similar to SVM with the advantage of more efficient classification evaluation due to a smaller set of support vectors with comparable errors. The RVM employs a Bayesian kernel technique using regression to make probabilistic predictions for classification. Its main disadvantage is that unlike SVM it does not give rise to a convex optimization problem, so that local minimums can occur, and global optimization cannot generally be guaranteed. Each of the algorithms mentioned can be used by medical analyzer 114 and can easily be tested, once the feature space has been defined and determined.

7. Additional Embodiments

While embodiments of the present disclosure are discussed above with reference to diagnosing traumatic brain injury, it should be understood that embodiments of the present disclosure are applicable to a wide variety of diagnostic systems and methods.

For example, in an embodiment, medical analyzer 114 can be used to diagnose breast cancer. In an embodiment, MRI scanner 102 or 202 is used to perform a mammogram on a patient. In an embodiment, the patient puts her breasts in two cylinders having receive coils, and MRI scanner 102 or 202 can perform MRI, MRE, and/or DTI scans on the patient's breasts and send the results to medical analyzer 114 for further analysis.

Further, in an embodiment, step 310 in FIG. 3 (i.e., determining whether the FA metric is less than 0.2) is optional. For example, in an embodiment, the 0.2 threshold for the FA metric is used to determine whether the FA is so low that no water diffusion is present in the tissue (e.g., in an embodiment, brain tissue). This typically occurs when the FA value is less than 0.2, but other metrics can be used in accordance with embodiments of the present disclosure. In an embodiment, medical analyzer 114 can use a variety of metrics and/or techniques to determine whether to perform isotropic inversion or anisotropic inversion. For example, in an embodiment, medical analyzer 114 can be configured to determine, based on the information from MRI scanner 102 or 202, whether a metric for determining stiffness (e.g., water diffusion and/or other stiffness metrics) in the tissue being examined is below a predetermined threshold. In an embodiment, this threshold can be configured (e.g., by a user, software, and/or manufacturer of medical analyzer 114). For example, in an embodiment, this threshold can be adjusted based on the tissue being analyzed.

In an embodiment, medical analyzer 114 can be used to detect the presence of a variety of abnormalities in the body. For example, many abnormalities in the body can be detected by observing irregular stiffness in tissue. Embodiments of the present disclosure can be used to detect this abnormal stiffness and determine regions of the body that have potential irregularities. For example, embodiments of the present disclosure can be used to diagnose Amyotrophic Lateral Sclerosis (ALS), heart disease, and cancerous tumors, among other irregularities.

Figure 6:
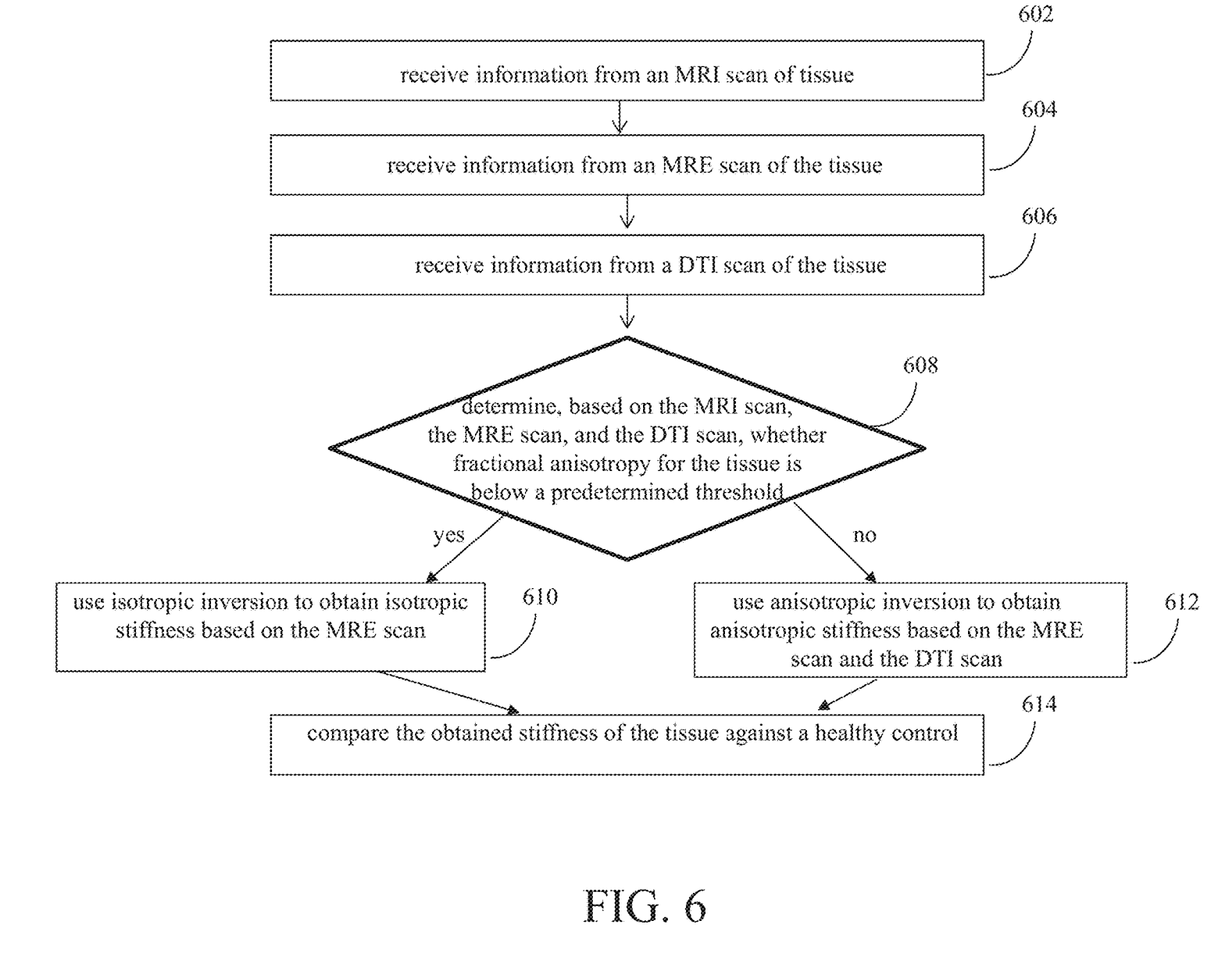
FIG. 6 is a flowchart of a method for diagnosing irregularities in tissue in accordance with an embodiment of the present disclosure.

FIG. 6 is a flowchart of a method for diagnosing irregularities in tissue in accordance with an embodiment of the present disclosure. In step 602, information is received from an MRI scan of tissue. For example, in an embodiment, medical analyzer 114 receives information from magnetic resonance imager 108. In step 604, information is received from an MRE scan of tissue. For example, in an embodiment, medical analyzer 114 receives information from magnetic resonance elastographer 112. In step 606, information is received from a DTI scan of tissue. For example, in an embodiment, medical analyzer 114 receives information from diffusion tensor imager 110. In step 608, a determination is made, based on the MRI scan, the MRE scan, and the DTI scan, whether fractional anisotropy for the tissue is below a predetermined threshold. For example, in an embodiment, medical analyzer 114 determines whether water diffusion in the tissue has a preferred direction, as indicated by metrics such as the FA metric or other metrics as discussed above.

In step 610, if the FA metric is below the predetermined threshold, isotropic inversion is used to obtain isotropic stiffness based on the MRE scan. For example, in an embodiment, medical analyzer 114 performs isotropic inversion on data from the MRE scan to determine isotropic stiffness of the tissue. In step 612, if the FA metric is not below the predetermined threshold, anisotropic inversion is used to obtain isotropic stiffness based on the MRE scan and the DTI scan. For example, in an embodiment, medical analyzer 114 performs anisotropic inversion on data from the MRE scan and the DTI scan to determine anisotropic stiffness of the tissue. In step 614, the obtained stiffness of the tissue is compared against a healthy control. For example, in an embodiment, medical analyzer 114 compares the stiffness of the tissue against stiffness in a healthy control of a healthy patient or against known stiffness values that are within a known healthy range (e.g., in an embodiment, based on the patient's age, height, weight, and/or known preexisting conditions).

Further, in an embodiment, medical analyzer 114 can use machine learning techniques to improve accuracy of the diagnosis as additional tests are performed. For example, in an embodiment, medical analyzer 114 can perform multiple scans of a variety of tissue types and can use machine learning to adjust diagnostic tests performed for a variety of tissue types. For example, in an embodiment, medical analyzer 114 can be configured to adjust metrics (e.g., FA and/or other metrics) for different tissues (and/or different sections of tissue within a tissue being examined, such as different brain sections) based on the accuracy of past diagnoses.

8. Exemplary Algorithms

To evaluate the stiffness in different brain regions, the proper inversion algorithm should be implemented. In isotropic regions such as gray matter, the wave velocity is the same in every direction of propagation. In anisotropic regions such as white matter, there can be three wave velocities in any direction of propagation, and these velocities can vary as a function of the direction of propagation as provided by the Christoffel equation.

It has been demonstrated previously that the viscoelastic parameters of an isotropic medium can be obtained from MRE measurements using an inversion of an isotropic Helmholtz equation. The evaluation of the stiffness parameters of an anisotropic medium requires an anisotropic material model, and additionally requires knowledge of the fiber pathway orientation, which is typically obtained using Diffusion Tensor Imaging (DTI).

Waveguide Elastography (WGE) introduces a method for evaluating the anisotropic properties of white matter in the human brain, in vivo. The approach utilizes a fusion of MRE, DTI, and an orthotropic anisotropic dynamical model, and was initially applied to the analysis of the CSTs in 5 healthy volunteers. Subsequently, it was applied in the study of the effects of neurodegeneration in 28 volunteers, 14 of whom were patients who had been diagnosed with ALS and 14 of whom were healthy age matched controls, and in the classification of the anisotropic properties of 12 white matter structures in one healthy control.

Embodiments of the present disclosure provide a recently developed approach called Mixed-Model Inversions (MMI) which uses a data driven binary indicator for the implementation of either an isotropic or anisotropic inversion algorithm based on the values of local Fractional Anisotropy (FA) values. For FA values less than 0.2, an isotropic medium is indicated, and an appropriate isotropic inversion algorithm is implemented. For FA values greater than or equal 0.2, anisotropic media are indicated, and an orthotropic anisotropic algorithm is implemented. Embodiments of the present disclosure provide a diagnostic methodology for the evaluation of brain health or pathology provided by the comparison of the brain stiffness of TBI patients with those of healthy controls.

Very consistent results indicate the particular class of anisotropy and associated stiffness coefficients of each of the structures in the brains of both the patients and the healthy cohort, providing features that may potentially be used as diagnostic metrics for the evaluation of brain health or pathology. The evaluation of the anisotropic properties of white matter structures in healthy controls has been shown to be important in the diagnosis of various diseases such as ALS, where significant variations in these properties can be observed. In TBI, injury to white matter structures can lead to a remodeling of the anisotropy (meaning a transition from a lower order anisotropy to a higher order anisotropy), as well as a complete transition from anisotropy to isotropy for severe trauma. Therefore, the study of baseline anisotropic models could be quite significant in the detection of different pathological conditions when variations from these healthy models are observed.

In an embodiment, the anisotropic material inversion spatially filters the MRE wave components and applies a Helmholtz decomposition along a local reference frame defined by the local DTI vectors to separate the total displacement fields into their longitudinal and transverse components. In an embodiment, upon performing a spatial-spectral filter along the local coordinate axes with specified k-space bandwidths, the equations of motion decouple, allowing for the evaluation of each of the orthotropic stiffness coefficients independently of the others.

Using an orthotropic model, there are single equations of motion for the longitudinal stiffness coefficients, C11, C22, and C33, and there are two equations of motion for each of the shear coefficients C44, C55, and C66. Previously, the solutions for the two equations for each of the coefficients C44, C55, and C66 were solved for separately, and the averages over the two solutions for each of the shear coefficients provided the result. In an embodiment of the present disclosure, these latter sets of equations are solved by using rotations about the principal local axis in an attempt to simultaneously minimize the Euclidian distance between the sets of solutions. This "rotational optimization" step provides a unique local reference frame for determining the stiffness coefficients and significantly reduces the variability of the shear coefficients when measured over the entire brain.

In an embodiment, there are additionally two equations of motion associated with each of the off-diagonal stiffness terms, C12, C13, and C23, and a similar minimization strategy is utilized for their solution. Specifically, having previously solved for C11, C22, C33, C44, C55, and C66, these are then utilized as known stiffness values in the remaining six equations of motion. However, here, the angles between the principal axes are rotated to separately minimize the Euclidian distance between the sets of solutions for C12, C13, and C23. The efficiency and accuracy of the minimization were improved by performing a global optimization using Brent's Algorithm, as opposed to minimizing over a fixed set of angles.

In an embodiment, the inversions are performed over each voxel within the brain, and white matter segmentation masks are then utilized for the extraction of the stiffness coefficients included in each mask. When performing studies including both gray and white matter regions, we utilize a method called a Mixed-Model Inversion (MMI), which utilizes a data-driven threshold provided by FA values which delineate between these regions and dictates whether an isotropic inversion algorithm or an anisotropic inversion algorithm is implemented with the appropriate k-space filter bandwidths. Specifically, for regions where FA<0.2, this typically indicates gray matter (isotropic regions), and for FA≥0.2, this typically indicates white matter (anisotropic regions).

In an embodiment, for the anisotropic inversions, a k-space bandwidth from 10-100 (rad/m) (with a Δk=1 rad/m) was utilized for the longitudinal stiffness coefficients (C11, C22, C33, C12, C13, and C23), and a bandwidth from 110-220 (rad/m) (with a Δk=1 rad/m) was utilized for the shear stiffness coefficients (C44, C55, and C66). These k-space bandwidths were obtained using the principal frequency estimation method to identify the dominant wave components for both the longitudinal and shear waves. Additionally, the volume utilized for the local spatial-spectral filter was 17×17×17 pixels optimized from the principal frequency estimation. For the isotropic inversions, the local spatial-spectral filter is identical to the anisotropic volume, however the k-space bandwidth for the shear waves is from 200-300 (rad/m) (with a Δk=1 rad/m).

In an embodiment, a fully orthotropic inversion model comprised of nine coefficients is used to analyze white matter in the human brain for several reasons. First, rather than solve for the anisotropic coefficients simultaneously using a coupled set of equations in a global reference frame as other approaches do, we chose to utilize directional filtering, a spatial-spectral filter (which appears as a spatially dependent Radon transform), and a Helmholtz decomposition in the local reference frame dictated by the DTI measurements, thereby allowing a decoupling of the equations of motion permitting a solution of each of the coefficients independently of the others. This approach has been found to be much less sensitive to noise than solutions using coupled sets of equations, and is additionally less sensitive to ill-conditionedness induced when there is a large disparity between the stiffness values comprising the anisotropic tensor in the presence of noise.

Additionally, as mentioned above, this avoids the use of a Bond Transformation (which is computationally intensive), since we are inverting in the local reference frame. Secondly, the orthotropic system is the highest order anisotropic model that allows for the complete decoupling of the equations of motion when using the spatial-spectral filtering. This permits the investigation of higher order anisotropy of unknown biological media without an imposition or limitation on the degree of anisotropy allowed. That is to say that we do not restrict our model to be simply transversely isotropic. Third, once our nine coefficients have been solved for, redundancies between the values within the orthotropic tensor components expose potentially lower order models to be valid. Therefore, rather than restrict our model to initially being of lower order anisotropy, we begin with a higher order anisotropy and allow the structure of the tensor to dictate which order model is appropriate.

Exemplary algorithms used by a medical analyzer in accordance with an embodiment of the present disclosure will now be discussed in greater detail. In an embodiment, we begin by defining global coordinates using the usual Cartesian (x,y,z) coordinates in Equation (1).

$$x_g = (x,y,z) = xe_1 + ye_2 + ze_3 \tag{1}$$

In Equation (1), $e_1$, $e_2$, $e_3$ are unit vectors in the x, y, z directions, respectively. We also will consider the representation of vectors in local frames with unit orthonormal vectors $n_1$, $n_2$, $n_3$, as shown by Equation (2).

$$u = (u_1, u_2, u_3) + u_2 n_2 + u_3 n_3 \tag{2}$$

The conversion from global to local coordinates is given by Equation (3).

$$u_i = (u_g \cdot n_i) \text{ for } i=1,2,3. \tag{3}$$

Since we deal with discrete locations in a voxel space, we also use bold notation for vector indices, so that $j=(j_x,j_y,j_z)$ denotes the index of a voxel associated to the location $r_1=(j_x d, j_y d, j_z d)$ where d is the size of the voxel (which for now is assumed to be a cube).

Let $\tilde{u}(t_n, r)$ denote the displacement at location r at discretely sampled times $t_n = n\Delta t$ where $n=0, \ldots, N_T-1$ is the index ranging over one time period=$N_T \Delta t$. We use the Fourier transform in time to obtain Equation (4) at the desired angular frequency $$\omega = \frac{2\pi}{T}.$$

$$u_g(\omega, r) = \Delta t \sum_{n=0}^{N-1} \tilde{u}(t_n, r) e^{-i\omega t_n} \tag{4}$$

Since we only deal with this frequency, the dependence is dropped from the notation $u_g(r) = u_g(\omega, r)$. Since the DTI data is given at voxel locations, we describe the inversions at a single voxel location $r_m$. Transverse and longitudinal spectrally filtered displacements in a direction n at voxel $r_m$ are defined using Equations (5) and (6) respectively, where W(m) represents a set of voxel indices over which the filter is applied.

$$u_{SF}^T(r_m, n) = -\frac{d^3}{2\pi} \Delta k n \times \left[ n \times \left( \sum_{j \in W(m)} \sum_{k=K_{min}^T}^{K_{max}^T} u_g(r_m) e^{-ikn \cdot (r_m - r_j)} \right) \right], \tag{5}$$

$$u_{SF}^L(r_m, n) = -\frac{d^3}{2\pi} \Delta k n \left[ n \cdot \left( \sum_{j \in W(m)} \sum_{k=K_{min}^L}^{K_{max}^L} u_g(r_m) e^{-ikn \cdot (r_m - r_j)} \right) \right], \tag{6}$$

For example, as shown by Equation (7), $$w(m) = \{j = (j_x, j_y, j_z) | |j_x - m_x| \le N_x^w, |j_y - m_y| \le N_y^w, |j_z - m_z| \le N_z^w\} \tag{7}$$

The index k corresponds to the magnitude of the wave vector in the direction n, and is limited depending on the expected wavelengths in their respected transverse or longitudinal directions. The terms $u_{SF}^T(r_m, n)$ and $u_{SF}^L(r_m, n)$ are defined in the global reference frame and are projected onto a local frame with basis $n_1$, $n_2$, $n_3$ (depending on the voxel index m) using Equation (3), namely, as shown by Equation (8):

$$u_\alpha^T(n_\gamma) = u_{SF}^T(r_m, n_\gamma) \cdot n_\alpha \text{ for } \alpha, \gamma = 1, 2, 3, \tag{8}$$

In Equation (8), we have set $n = n_\gamma$, (one of our coordinate directions). From elementary vector identities, it follows that $u_\alpha^T(n_\alpha) = 0$ for $\alpha = 1, 2, 3$. Under monochromatic excitation, with the assumption that $n_3$ is the principal direction of the fiber tracts of an orthotropic elastic medium, the following relationships hold where the superscripts A and B correspond to the equations of motion for the same coefficient along the respective axes $n_1$, $n_2$, and $n_3$, as shown by Equations (9).

$$C_{4,4}^A = -\rho\omega^2 \frac{u_3^T(n_2)}{\left(\frac{\partial^2 u_3^T}{\partial x_2^2}(n_2)\right)} \quad C_{4,4}^B = -\rho\omega^2 \frac{u_2^T(n_3)}{\left(\frac{\partial^2 u_2^T}{\partial x_3^2}(n_3)\right)} \tag{9}$$

$$C_{5,5}^A = -\rho\omega^2 \frac{u_3^T(n_1)}{\left(\frac{\partial^2 u_3^T}{\partial x_1^2}(n_1)\right)} \quad C_{5,5}^B = -\rho\omega^2 \frac{u_1^T(n_3)}{\left(\frac{\partial^2 u_1^T}{\partial x_3^2}(n_3)\right)}$$

$$C_{6,6}^A = -\rho\omega^2 \frac{u_2^T(n_1)}{\left(\frac{\partial^2 u_2^T}{\partial x_1^2}(n_1)\right)} \quad C_{6,6}^B = -\rho\omega^2 \frac{u_1^T(n_2)}{\left(\frac{\partial^2 u_1^T}{\partial x_2^2}(n_2)\right)}$$

The derivative terms are obtained using Equation (8) with Equation (5) by replacing $r_m$ with the independent (local) vector variable $x = x_1 n_1 + x_2 n_2 + x_3 n_3$, and then differentiating with the local basis $(n_1, n_2, n_3)$ held fixed. For example, for the derivatives in (A8) with $\alpha, \gamma = 1, 2, 3$:

$$\frac{\partial^2 u_\alpha^T(n_\gamma)}{\partial x_\gamma^2} = \frac{\partial^2 (u_{SF}^T(x, n_\gamma) \cdot n_\alpha)}{\partial x_\gamma^2} = -\frac{d^3}{2\pi}\Delta k \tag{10}$$

$$\left\{ n_\gamma \times \left[ n_\gamma \times \left( \sum_{j \in W(m)} \sum_{k=K_{min}^T}^{K_{max}^T} (ik(n_\gamma \cdot n_\gamma))^2 u(r_j) e^{ikn_\gamma \cdot (x-r_j)} \right) \right] \right\} \cdot n_\alpha = $$

$$\frac{d^3}{2\pi}\Delta k \left\{ n_\gamma \times \left[ n_\gamma \times \left( \sum_{j \in W(m)} \sum_{k=K_{min}^T}^{K_{max}^T} k^2 u(r_j) e^{ikn_\gamma \cdot (x-r_j)} \right) \right] \cdot n_\alpha \right\}$$

Since we approximate the derivatives using truncated spatial Fourier transforms, the "A" and "B" values cannot be expected to be exactly identical computationally. Furthermore, the orthogonal vectors $n_1$ and $n_2$ are arbitrary to a rotational angle. That is, given an arbitrary pair of vectors, $n_{1,0}$, $n_{2,0}$ orthonormal to $n_3$, we define $n_1(\psi) = \cos\psi n_{1,0} + \sin\psi n_{2,0}$, and $n_2(\psi) = -\sin\psi n_{1,0} + \cos\psi n_{2,0}$.

By allowing this rotation, the value $\psi$ and hence $n_1$ and $n_2$ can be selected such that the error between the "A" and "B" values are minimized. More concisely, we select $$\psi_0 = \arg\min_{0 \le \psi \le 2\pi} \left( |C_{4,4}^A(\psi) - C_{4,4}^B(\psi)|^2 + \right. \tag{11}$$

$$\left. |C_{5,5}^A(\psi) - C_{5,5}^B(\psi)|^2 + |C_{6,6}^A(\psi) - C_{6,6}^B(\psi)|^2 \right)$$

We set $C_{\alpha,\alpha} = (C_{\alpha,\alpha}^A(\psi_0) + C_{\alpha,\alpha}^B(\psi_0))/2$ for $\alpha = 4, 5, 6$. The minimization problem is approximated using Brent's algorithm within each subdivision (usually 32) of the interval $[0, 2\pi]$. Once $\psi_0$ is determined, $n_1 = n_1(\psi_0)$ and $n_2 = n_2(\psi_0)$ are set for the determination of the remainder of the coefficients, namely, $$C_{1,1} = -\rho\omega^2 \frac{u_1^L(n_1)}{\left(\frac{\partial^2 u_1^L}{\partial x_1^2}(n_1)\right)} \tag{12}$$

$$C_{2,2} = -\rho\omega^2 \frac{u_2^L(n_2)}{\left(\frac{\partial^2 u_2^L}{\partial x_2^2}(n_2)\right)}$$

$$C_{3,3} = -\rho\omega^2 \frac{u_3^L(n_3)}{\left(\frac{\partial^2 u_3^L}{\partial x_3^2}(n_3)\right)}$$

For the specific longitudinal mode, we first focus on the determination of coefficient $C_{12}$. Let $$n_{1,2} = n_{1,2}(\theta) = \cos(\theta) n_1 + \sin(\theta) n_2 \tag{13}$$

be a propagation direction which lies in the $n_1$, $n_2$ plane. Along this (local) direction, we have $$C_{11}\frac{\partial^2 u_1^L(n_{1,2})}{\partial x_1^2} + C_{66}\frac{\partial^2 u_1^L(n_{1,2})}{\partial x_2^2} + (C_{12} + C_{66})\frac{\partial^2 u_2^L(n_{1,2})}{\partial x_1 \partial x_2} = \tag{14}$$

$$-\rho\omega^2 u_1^L(n_{1,2})$$

$$C_{22}\frac{\partial^2 u_2^L(n_{1,2})}{\partial x_2^2} + C_{66}\frac{\partial^2 u_2^L(n_{1,2})}{\partial x_1^2} + (C_{12} + C_{66})\frac{\partial^2 u_1^L(n_{1,2})}{\partial x_1 \partial x_2} = $$

$$-\rho\omega^2 u_2^L(n_{1,2}).$$

Differentiating as before (by replacing $r_m$ with the independent (local) vector variable $x = x_1 n_1 + x_2 n_2 + x_3 n_3$, and then differentiating Equation (6) with the local basis $(n_1, n_2, n_3)$ fixed, we obtain $$\frac{\partial^2 u_\delta^L(n)}{\partial x_\alpha \partial x_\beta} = D_2(n)\{(n \cdot n_\delta)(n \cdot n_\alpha)(n \cdot n_\beta)\} \tag{15}$$

for any unit vector n and any indices $\delta = 1, 2, 3$ $\alpha = 1, 2, 3$ $\beta = 1, 2, 3$, where $$D_2(n) = \frac{d^3}{2\pi}\Delta k n \cdot \left( \sum_{j \in W(m)} \sum_{k=K_{min}^L}^{K_{max}^L} k^2 u(r_j) e^{ikn \cdot (r_m - r_j)} \right). \tag{16}$$

Setting $n = n_{1,2} = \cos(\theta) n_1 + \sin(\theta) n_2$ in Equation (15) so that $n \cdot n_1 = \cos(\theta)$ and $n \cdot n_2 = \sin(\theta)$ gives $$\frac{\partial^2 u_2^L(n_{1,2})}{\partial x_1 \partial x_2} = D_2(n_{1,2})\{\cos(\theta) \sin^2(\theta)\} = \frac{\partial^2 u_1^L(n_{1,2})}{\partial x_2^2} \tag{17}$$

$$\frac{\partial^2 u_1^L(n_{1,2})}{\partial x_1 \partial x_2} = D_2(n_{1,2})\{\cos^2(\theta) \sin(\theta)\} = \frac{\partial^2 u_2^L(n_{1,2})}{\partial x_1^2} \tag{18}$$

This is used in Equation (13) to obtain two expressions for $C_{12}$, namely, $$(C_{1,2}(\theta))^A = -2C_{66} - \frac{\rho\omega^2 D_0 + C_{11} D_2 \cos^2\theta}{D_2 \sin^2\theta} \tag{19}$$

$$(C_{1,2}(\theta))^B = -2C_{66} - \frac{\rho\omega^2 D_0 + C_{22} D_2 \sin^2\theta}{D_2 \cos^2\theta} \tag{20}$$

In Equations (19) and (20, $D_0 = D_0(n_{1,2}(\theta))$ is computed using $$D_0(n) = -\frac{d^3}{2\pi}\Delta k n \cdot \left( \sum_{j \in W(m)} \sum_{k=K_{min}^L}^{K_{max}^L} u(r_j) e^{ikn \cdot (r_m - r_j)} \right) \tag{21}$$

$D_2 = D_2(n_{1,2}(\theta))$ is defined in Equation (15). Note that $D_0(n)$ is the scalar factor of n in the definition of $u_{SF}^L(r_m, n)$. Analagous to our determination of $\psi_0$, we define $$\theta_{1,2} = \arg\min_{0 \le \theta < 2\pi} |(C_{1,2}(\theta))^A - (C_{1,2}(\theta))^B|^2 \tag{22}$$

$$C_{1,2} = \frac{1}{2}((C_{1,2}(\theta_{1,2}))^A + (C_{1,2}(\theta_{1,2}))^B). \tag{23}$$

This process is repeated for the determination of $C_{1,3}$ and $C_{2,3}$. In general, for the 3 pairs of indices $(\alpha,\beta) = (1,2), (1,3), (2,3)$, set $\gamma = 9 - \alpha - \beta$. Then $$(C_{\alpha,\beta}(\theta))^A = -2C_{\gamma,\gamma} - \frac{\rho\omega^2 D_0(n_{\alpha,\beta}(\theta)) + C_{\alpha,\alpha} D_2(n_{\alpha,\beta}(\theta))\cos^2\theta}{D_2(n_{\alpha,\beta}(\theta))\sin^2\theta}$$

$$(C_{\alpha,\beta}(\theta))^B = -2C_{\gamma,\gamma} - \frac{\rho\omega^2 D_0(n_{\alpha,\beta}(\theta)) + C_{\beta,\beta} D_2(n_{\alpha,\beta}(\theta))\sin^2\theta}{D_2(n_{\alpha,\beta}(\theta))\cos^2\theta}$$

$$\theta_{\alpha,\beta} = \arg\min_{0 \le \theta < 2\pi} |(C_{\alpha,\beta}(\theta))^A - (C_{\alpha,\beta}(\theta))^B|^2 \tag{24}$$

$$C_{\alpha,\beta} = \frac{1}{2}((C_{\alpha,\beta}(\theta_{\alpha,\beta}))^A + (C_{\alpha,\beta}(\theta_{\alpha,\beta}))^B). \tag{25}$$

The structure for exemplary orthotropic, tetragonal, and hexagonal elastic tensors are shown below. An orthotropic system has 9 independent coefficients. Tetragonal systems (classes 4 mm, 422, $\bar{4}$2m, and 4/mmm) are subsets of orthotropic systems with the properties ($C_{11}=C_{22}$, $C_{13}=C_{23}$, $C_{44}=C_{55}$), thereby having 6 independent coefficients. The hexagonal system (also called transversely isotropic) has the additional property that $$\left( C_{66} = \frac{C_{11} - C_{12}}{2} \right),$$

reducing the independent coefficients to 5. Specifically, matrix (26) below shows orthotropic tensors, matrix (27) shows tetragonal tensors, and matrix (28) shows hexagonal tensors.

$$\begin{bmatrix} C_{11} & C_{12} & C_{13} & 0 & 0 & 0 \\ C_{12} & C_{22} & C_{23} & 0 & 0 & 0 \\ C_{13} & C_{23} & C_{33} & 0 & 0 & 0 \\ 0 & 0 & 0 & C_{44} & 0 & 0 \\ 0 & 0 & 0 & 0 & C_{55} & 0 \\ 0 & 0 & 0 & 0 & 0 & C_{66} \end{bmatrix} \tag{26}$$

$$\begin{bmatrix} C_{11} & C_{12} & C_{13} & 0 & 0 & 0 \\ C_{12} & C_{11} & C_{13} & 0 & 0 & 0 \\ C_{13} & C_{13} & C_{33} & 0 & 0 & 0 \\ 0 & 0 & 0 & C_{44} & 0 & 0 \\ 0 & 0 & 0 & 0 & C_{44} & 0 \\ 0 & 0 & 0 & 0 & 0 & C_{66} \end{bmatrix} \tag{27}$$

$$\begin{bmatrix} C_{11} & C_{12} & C_{13} & 0 & 0 & 0 \\ C_{12} & C_{11} & C_{13} & 0 & 0 & 0 \\ C_{13} & C_{13} & C_{33} & 0 & 0 & 0 \\ 0 & 0 & 0 & C_{44} & 0 & 0 \\ 0 & 0 & 0 & 0 & C_{44} & 0 \\ 0 & 0 & 0 & 0 & 0 & \frac{C_{11} - C_{12}}{2} \end{bmatrix}. \tag{28}$$

Formulas for eigenvalue based anisotropic metrics and diffusivities are shown below. The eigenvalues are ordered so that $\lambda_1 \ge \lambda_2 \ge \lambda_3 \ge 0$, and $\bar{\lambda} = (\lambda_1 + \lambda_2 + \lambda_3)/3$ is the mean. The FA, relative anisotropy (RA), and volume ratio (VR) are non-dimensional measures given by Equations (29)-(31).

$$FA = \sqrt{\frac{3\sum_{i=1}^{3}(\lambda_i - \bar{\lambda})^2}{2\sum_{i=1}^{3}\lambda_i^2}} \tag{29}$$

$$RA = \frac{\sqrt{\frac{1}{3}\sum_{i=1}^{3}(\lambda_i - \bar{\lambda})^2}}{\bar{\lambda}} \tag{30}$$

$$VR = \frac{\lambda_1 \lambda_2 \lambda_3}{\bar{\lambda}^3} \tag{31}$$

The parallel, mean, and radial diffusivities have units of (length$^2$/time) and are given by Equations (32)-(34).

$$PD = \lambda_1 \tag{32}$$

$$MD = \bar{\lambda} \tag{33}$$

$$RD = \frac{\lambda_2 + \lambda_3}{2} \tag{34}$$

Measures of the shape of the diffusion ellipsoids shown in FIGS. 3-6 are also non-dimensional and can be described by linear anisotropy ($C_l$), which approaches unity for long cigar-shaped ellipsoids, planar anisotropy ($C_p$) for flattened speheroids, and spherical symmetry ($C_s$) for the isotropic spherical case. Note that $C_l + C_p + C_s = 1$, so that $C_a = 1 - C_s$ is an additional anisotropy measure which relates to the deviation from the spherical case. Specifically, these are given by Equations (35)-(38).

$$C_l = \frac{\lambda_1 - \lambda_2}{\lambda_1 + \lambda_2 + \lambda_3} \quad (35)$$

$$C_p = \frac{2(\lambda_2 - \lambda_3)}{\lambda_1 + \lambda_2 + \lambda_3} \quad (36)$$

$$C_s = \frac{3\lambda_3}{\lambda_1 + \lambda_2 + \lambda_3} \quad (37)$$

$$C_a = \frac{\lambda_1 + \lambda_2 - 2\lambda_3}{\lambda_1 + \lambda_2 + \lambda_3} \quad (38)$$

9. Conclusion

It is to be appreciated that the Detailed Description, and not the Abstract, is intended to be used to interpret the claims. The Abstract may set forth one or more but not all exemplary embodiments of the present disclosure as contemplated by the inventor(s), and thus, is not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Any representative signal processing functions described herein can be implemented using computer processors, computer logic, application specific integrated circuits (ASIC), digital signal processors, etc., as will be understood by those skilled in the art based on the discussion given herein. Accordingly, any processor that performs the signal processing functions described herein is within the scope and spirit of the present disclosure.

The above systems and methods may be implemented as a computer program executing on a machine, as a computer program product, or as a tangible and/or non-transitory computer-readable medium having stored instructions. For example, the functions described herein could be embodied by computer program instructions that are executed by a computer processor or any one of the hardware devices listed above. The computer program instructions cause the processor to perform the signal processing functions described herein. The computer program instructions (e.g., software) can be stored in a tangible non-transitory computer usable medium, computer program medium, or any storage medium that can be accessed by a computer or processor. Such media include a memory device such as a RAM or ROM, or other type of computer storage medium such as a computer disk or CD ROM. Accordingly, any tangible non-transitory computer storage medium having computer program code that cause a processor to perform the signal processing functions described herein are within the scope and spirit of the present disclosure.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments.

What is claimed is:

1. A system for diagnosing brain pathologies, the system comprising:
    a magnetic resonance imaging (MRI) scanner, comprising:
        a magnetic resonance imager configured to generate an MRI scan of a brain of a patient,
        a magnetic resonance elastographer (MRE) configured to measure elastic vibration of the brain, and
        a diffusion tensor imager configured to:
            generate a diffusion tensor imaging (DTI) scan of the brain, and
            generate DTI eigenvectors and eigenvalues based on the DTI, and
            generate a fractional anisotropy (FA) metric based on the DTI scan; and
    a medical analyzer configured to:
        receive the MRI scan, the elastic vibration, the DTI scan, the eigenvectors, the eigenvalues, and the FA metric,
        determine whether the FA metric is less than 0.2,
        in response to a determination that the FA metric is less than 0.2:
            determine isotropic brain stiffness based on the elastic vibration, and
            determine, based on the eigenvectors and eigenvalues, a stiffness of white matter segments of the brain,
        in response to a determination that the fractional anisotropy is greater than or equal to 0.2:
            determine anisotropic brain stiffness based on the elastic vibration and the DTI scan, and
            determine, based on the eigenvectors and eigenvalues, a stiffness of grey matter segments of the brain,
        compare the stiffness of the grey matter segments or the white matter segments with corresponding segments in a healthy control, and
        determine a brain trauma or pathology based on differences in stiffnesses of the grey matter segments or the white matter segments with the corresponding segments in the healthy control.

2. The system of claim 1, wherein the MRI scanner is further configured to determine longitudinal and transverse precessions of atoms in the brain.

3. The system of claim 2, wherein the MRI scanner is configured to generate longitudinal relaxation (T1) and transverse relaxation (T2) images based on the precessions of atoms in the brain.

4. The system of claim 3, wherein the medical analyzer is further configured to identify segments of the brain based on the DTI scan and the T1 and T2 images.

5. The system of claim 1, wherein the medical analyzer is further configured to:
compare the stiffness of segments of the brain against a healthy control; and
determine whether the brain exhibits brain trauma or pathology based on the comparison.

6. The system of claim 5, wherein the medical analyzer is further configured to determine, based on the comparison, which regions of the brain are healthy and which regions of the brain are unhealthy.

7. The system of claim 1, wherein the medical analyzer is configured to determine stiffness of segments of the brain using a mixed-model inversion (MMI) method.

8. The system of claim 7, wherein the MMI method comprises 22 metrics, including MRI metrics, diffusion metrics, isotropic metrics, and anisotropic metrics.

9. The system of claim 1, wherein the medical analyzer is further configured to segment isotropic and anisotropic segments of the brain.

10. The system of claim 9, wherein the medical analyzer is further configured to:
train a classifier using the segmented isotropic and anisotropic segments of the brain.

11. The system of claim 1, wherein the medical analyzer is further configured to determine anisotropic brain stiffness by:
spatially filtering MRE wave components measured by the MRE, and
separating displacement fields in the MRE wave components into longitudinal and transverse components.

12. The system of claim 11, wherein the medical analyzer is further configured to:
apply a Helmholtz decomposition along a local reference frame defined by local DTI vectors to separate the displacement fields in the MRE wave components into longitudinal and transverse components.

13. The system of claim 11, wherein the medical analyzer is further configured to:
solve, based on the longitudinal and transverse components, equations of motion for longitudinal stiffness coefficients and shear coefficients using rotations about a principal local axis.

14. The system of claim 1, wherein the medical analyzer is further configured to determine, based on the comparison, which grey matter segments or white matter segments are healthy and which grey matter segments or white matter segments are unhealthy.

15. The system of claim 1, wherein the medical analyzer is configured to determine stiffness of grey matter segments or white matter segments using a mixed-model inversion (MMI) method.

16. The system of claim 15, wherein the MMI method comprises 22 metrics, including MRI metrics, diffusion metrics, isotropic metrics, and anisotropic metrics.

17. The system of claim 1, wherein the grey matter segments and the white matter segments comprise 145 different structures, and wherein the medical analyzer is further configured to compare the stiffness of the 145 different structures with corresponding structures in the healthy control.

* * * * *